United States Patent [19]

Radisson et al.

[11] Patent Number: 4,876,362

[45] Date of Patent: Oct. 24, 1989

[54] PROCESS FOR THE PREPARATION OF THIENYLETHYLAMINES

[75] Inventors: Joël Radisson, Toulouse; Emile Braye, Auterive, both of France

[73] Assignee: Sanofi, Paris, France

[21] Appl. No.: 132,070

[22] Filed: Dec. 11, 1987

[30] Foreign Application Priority Data

Dec. 23, 1986 [FR] France .................................. 8618101

[51] Int. Cl.$^4$ ................... C07D 409/00; C07D 333/12
[52] U.S. Cl. .......................................... 549/59; 549/74
[58] Field of Search ..................................... 549/59, 74

[56] References Cited

FOREIGN PATENT DOCUMENTS 2623174 12/1977 Fed. Rep. of Germany ........ 549/59

OTHER PUBLICATIONS

P. Popescu et al.: "Preparation of Ethylamines from Acetonitrile.1. Laboratory Study of the Preparation of a Selective Catalyst for Monethylamine", & Rev. Chim. (Bucharest) 1971, 22(6), 327–331, Chemical Abstracts, vol. 75, No. 21, p. 250 (Nov. 22, 1971).

RO-A-53 953 (Institual "Chimigaz") 29-11-1971, Chemical Abstracts, vol. 77, No. 19, (Nov. 6, 1972), p. 344, resume No. 125951q, Columbus, Ohio US.

JP-A-78 50 109 (Ashi Chemical Industry Co. Ltd.) 08-05-1978, Chemical Abstracts, vol. 89, No. 9, (Aug. 28, 1987), p. 395, Resume No. 75245e, Columbus, Ohio, US.

Primary Examiner—Mary C. Lee
Assistant Examiner—Robert C. Whittenbaugh
Attorney, Agent, or Firm—Wegner & Bretschneider

[57] ABSTRACT

The invention has as its subject a process for the preparation of thienylethylamines of the formula

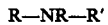

where R represents the group

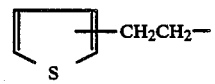

and R' represents hydrogen or a group identical to R, by catalytic hydrogenation of a compound of the formula

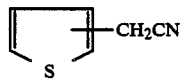

synthesis intermediates.

7 Claims, No Drawings

PROCESS FOR THE PREPARATION OF THIENYLETHYLAMINES

The present invention relates to a process for the preparation of thienylethylamines.

More particularly, the invention concerns a new method of synthesis of thienylethylamines represented by the formula:

R—NH—R'  (I)

in which R represents the group

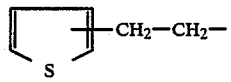

and R' represents an atom of hydrogen or a group identical to R.

This new method consists of the catalytic hydrogenation of nitriles of the general structure (II).

The compounds of formula (I) in which R' is hydrogen are well known in the literature and are used as intermediates in the preparation of derivatives used just as much in the chemical industry as in the pharmaceutical industry (for example FR-A-2 397 417 and 2 358 150).

The compounds of formula (I) in which R' represents a group identical to R are new, and constitute another aspect of the present invention.

The process for the preparation of the compounds of formula (I) where R' is hydrogen are described in the literature, for example:

reduction of the beta-nitrovinyl-2 or -3 thiophenes by the double hydride of lithium and aluminium (S. GRONOWITZ and E. SANDBERG, ARKIV for Kem, 1970, 32, 217–227) or by electrolytic method (FR-A-2 415 671):

CURTIUS degradation on the (thienyl-3)-3 proprionazide (E.

CAMPAIGNE at W. C. McCarty, J. Am Chem. Soc. 1954, 76, 4466–4467);

HOFFMAN degradation of the (thienyl -2)-3 propionamide (G. BARGER and A. P. T. EASSOU, J. Chem. Soc. 1938, 2100–2104);

amination of the haloethyl-2 or arylsulphonyloxyethyl-2 thiophenes, either directly (F. F. BLICKE and J. H. BURCKHALTER, J. Am. Soc. 9142, 64, 477–480) or by a phthalimide intermediate (FR-A-2 299 332).

All of these methods are difficult to employ on an industrial scale, either because the raw materials are difficult to obtain, as is the case with propionazides or amides for the CURTIUS or HOFFMAN degradations, or because the reagents are costly and/or dangerous to use, as is the case with the hydride of lithium and aluminium, or because of insufficient yields.

It is equally known that the (thienyl-2)-2 ethylamine and the (thienyl-3)-2 ethylamine can be prepared by the reduction of thiopheneacetonitriles with the hydride of lithium and aluminium (E. COMPAIGNE and W. C. Mc CARTY, J. Am. Chem. Soc. 1954, 76, 4466–4467 or with sodium in butanol at reflux (F. F. BLICKE and J. H. BURCKHALTER, J. Am. Chem. Soc. 1942, 64, 477–480), but these methods also present the problems indicated above.

The (thienyl-2)-2 ethylamine has been obtained by the electrochemical reduction of thiophene-2-acetonitrile with a maximum yield of only 25% (W. HERZ and L. TSAI, J. Am. Chem. Soc. 1955, 77, 3529–3531).

The catalytic hydrogenation of thienylacetonitrile has never been described, and it is known that sulphur in general and thiophene in particular inactivate to a large degree all the hydrogenation catalysts.

Nickel catalysts, for example, are rapidly poisoned (KUBOTA and Al. Jap. J. Chem. 2, 45, 1925) and even sulphuretted catalysts, known for being the most resistant to poisoning, quickly become inactive. In the same way, with molybdenum disulphide at 200° C. and under 200 atmospheres the conversion rate of thiophene to thiolane remains poor. (CAWLEY and Al. J. Soc. Chem. Ind. 62 116, 1943).

MOZIMGO (J. Am. Chem. Soc. 67, 2092 (1945) was able to effect the transformation of thiophene to thiolane with a yield of 70%, but by using 200% of palladium in relation to the substrate, which prohibits the transference of this method to the industrial scale.

It is also known that Raney nickel decomposes thiophene giving hydrogen sulphide and butane at 80° C. in ethanol (H. HAUPTMANN and Al. Chem. Rev. 62, 347, (1962) and "Thiophene and its derivatives" by H. D. HARTOUGH, p. 167 and 168, (1952), Interscience Publishers N.Y., in the series "The chemistry of Heterocyclic Compounds").

Finally, it is known (L. Kh. FREIDLIN and E. F. LITVIN, KHIMIYA g. and SOED 1967, 3, 22) that the catalytic hydrogenation of beta-nitrovinyl-2 thiophene only gives traces of thienylethylamine. Such a reaction is also disclosed in FR-A-2508456.

It has now been found that by using a catalyst with a nickel or cobalt base, it is possible to submit a thiopheneacetonitrile to hydrogenation to obtain thienylethylamines with very high yields.

It has equally been found that this type of hydrogenation a primary thienylethylamine and/or a secondary thienylethylamine is obtained, and that the reaction can be directed towards obtaining one or other of the two amines or towards an easily separable mixture of thienylethylamine and di(thienylethyl)amine.

So, the present invention has as its subject a process for the preparation of thienylethylamines of the following formula I and their addition salts with acids,

R—NH—R' in which R represents the group

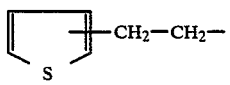

and R' represents a hydrogen atom or a group identical to R characterised in that the thienylacetonitrile of the formula

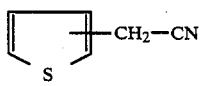

II in solution is submitted to a hydrogenation in the presence of a catalyst with a nickel or cobalt base, at a temperature between 15 and 80° C. and a pressure between ambiant pressure and 100 bars (between $10^5$ and $10^7$Pa) and the products thus obtained are optionally transformed into their addition salts.

The pressure can preferably be between 1 and 6 MPa.

The catalysts which are suitable for this hydrogenation are notably Raney nickel, nickel boride (R. Paul et al., Ind. Eng. Chem. 44 (5) 1006 (1952), nickel catalysts on an inert base, nickel according to URUSHIBARA (K. HATA, URUSHIBARA Catalyst, University of Tokyo Press, Tokyo 1971) and similar to the substrate.

The quantities of catalyst employed are of the order of 2 to 30% by weight in relation to the substrate.

The concentration of the substrate can vary a great degree; for economic reasons the operation is carried out at concentrations between 20 and 40% (w/v).

The substrate can be introduced into the reactional medium, in one go or as the reaction proceeds.

The solvent is entirely a standard organic solvent or a mixture of anhydrous or aqueous solvents able to dissolve the nitrile. which does not hydrogenate during the reaction and which does not lead to undesirable secondary products to the point of compromising the economic aspect of the process.

The solvent will preferably be an alcohol, particularly a light alcohol such as methanol or ethanol or an alkoxy-2-ethanol or -2-propanol or similar or one could also operate in a hydroalcoholic medium. Equally suitable are the ethers such as tetrahydrofuran, dioxan, the ethers of ethyleneglycol or other glycols and the aliphatic ethers.

The reactional medium can usefully be made acid by a solvent. The solvent could then be a carboxylic acid, pure and mixed with another solvent as long as it does not attack the catalyst, notable a mixture of acetic acid and an aliphatic alcohol with $C_1-C_4$ like ethanol, for example, in a ratio of 75-25.

When the calculated quantity of hydrogen is absorbed the primary thienylethylamine which passes over at a lower temperature is distilled off, and then the temperature is increased and the di(thienylethyl)amine is distilled off. The two amines can also be separated on the basis of the different solubilities of their salts. The hydrochloride of (thienyl-2)-2-ethylamine is very soluble in water, that of the di(thienyl-2)-2-ethyl is insoluble.

In order to favour the formation of the primary thienylethylamines the hydrogenation is effected in the presence of a vase such as an alkali metal hydroxide, notably NaOH, LiOH or an alkaline-earth metal hydroxide, ammonia, a quaternary ammonium hydroxide of the formula $HON(R_1)_4$ in which $R_1$ represents a $C_1-C_4$ alkyl, an alkali metal carbonate, such as sodium, potassium or cesium carbonate in quantities varying from 0.1% to 15% in ratio to the thienylacetonitrile used. In this way the hydrogenation can be directed towards obtaining the primary amine with yields of more than 80%. In certain cases, by choosing the opportune base, it is possible to obtain the primary amine almost exclusively.

The thienylethylamines thus obtained can be converted into their addition salts by treatment of a solution of the amine with the acid dissolved preferably in the same solvent.

The present invention therefore enables the preparation on an industrial scale of the primary thienylethylamines, for example, the (thienyl-2)-2-ethylamine, by a very simple and less onerous procedure, compared with the previous technique and therefore makes avaiable intermediate of synthesis which are very useful especially in the pharmaceutical industry.

The present invention equally makes it possible to obtain secondary thienylethylamines, for example, di((thienyl-2)-2 ethyl)amine and di((thienyl-3)-2 ethyl)amine which have never been isolated and their salts.

Thus, according to another aspect, the present invention concerns the compounds of the formula (I), in which R' is a group identical to R and their addition salts.

These products are also useful intermediates for the preparation of compounds with interesting pharmacological properties.

For example, by alkylation followed by a quaternisation compounds are obtained with an anti-bacterial activity.

The following non-limiting examples are given as an illustration of the present invention.

EXAMPLE 1 (Thienyl-2)-2 ethylamine 50 g of thienyl-2-acetonitrile, 200 ml of ethanol, 2.5 ml of 10 N sodium hydroxide and 10 g of Raney nickel are introduced into a 500 ml hydrogenator with magnetic agitation. The hydrogenation reaction takes place at 50° C. under a pressure of 30 bars (3 MPa).

The catalyst is then filtered, the alcohol evaporated and the thienylethylamine distilled at 90° C./15 mm Hg (2 kPa).

38 g of the product sought is thus obtained (Yield 74 %) of which the properties correspond to those given in the literature. EXAMPLE 2 (Thienyl-2)-2 ethylamine According to the process described in example 1, 44.95 of (thienyl-2)-2 ethylamine is obtained, by hydrogenating 50 g of thienyl-2 acetonitrile in 200 ml of ethanol in the presence of 10 g of Raney nickel, 2.5 ml of water and 3.5 g $K_2CO_3$, under a pressure between 15 and 22 bars (1.5 and 2.2 MPa). Yield 87%

EXAMPLE 3 (Thienyl-2)-2 ethylamine

According to the process described in example 1, 32.5 g of (thienyl-2)-2 ethylamine is obtained by introducing into the hydrogenator 50 g of thienyl-2 acetonitrile, 200 ml of ethanol, 5 ml of water, 12.5 g of tetramethylammonium hydroxide in 20% solution in methanol and 10 g of Raney nickel under a pressure 26 and 40 bars (2.6 and 4 MPa). Yield 65%

EXAMPLE 4 (Thienyl-2)-2 ethylamine

According to the process described in example 1, 35.9 g of (thienyl-2)-2 ethylamine is obtained by introducing into the hydrogenerator 50 g of thienyl-2 acetonitrile, 200 ml of ethanol, 10 ml of water, 5 g of lithium hydroxide and 10 g of Raney nickel, under a pressure between 26 and 40 bars (2.6 and 4 MPa). Yield 69.7%.

EXAMPLE 5 (Thienyl-2)-2 ethylamine

According to the process described in example 1, 50 g of thienyl-2 acetonitrile, 200 ml of isopropanol, 5 ml of water, 4 g of potassium carbonate and 10 g of Raney nickel under a pressure of between 28 and 40 bars (2.8 and 4 MPa) are introduced into the hydrogenerator. 40.7 g of (thienyl-2)-2 ethylamine is obtained. Yield 79%.

EXAMPLE 6 (Thienyl-2)-2 ethylamine 50 g of thienyl-2 acetonitrile, 200 ml of methanol, 10 g of Raney nickel and 1 g of sodium hydroxide are introduced into a 5 ml hydrogenation autoclave. After hydrogenation at 50° C. and under a pressure between 18 and 40 bars (1.8 and 4 MPa), according to the process in example 1, 41.8 g of (thienyl-2)-2 ethylamine is distilled. Yield 81%.

EXAMPLE 7 (Thienyl-2)-2 ethylamine

According to the process described in example 1, 32.1 g of (thienyl-2)-2 ethylamine is obtained, by hydrogenating 50 g of thienyl-2 acetonitrile in 150 ml of ethoxy-2 ethanol, in the presence of 10 g of Raney nickel and 3 g of $K_2CO_3$, under a pressure between 26 and 50 bars (2.6 and 5 MPa). Yield 62.5%.

EXAMPLE 8 (Thienyl-2)-2 ethylamine

According to the process described in example 1, 25.4 g of (thienyl-2)-2 ethylamine is obtained, by hydrogenating 50 g of thienyl-2 acetonitrile in 200 ml of ethanol, in the presence of 10 g of Raney nickel and 2.5 ml of a 40 % solution of potassium hydroxide under a pressure between 15 and 40 bars (1.5 and 4 MPa). Yield 49%.

EXAMPLE 9 (Thienyl-2)-2 ethylamine

According to the process described in example 1, 26.5 g of (thienyl-2)-2 ethylamine is obtained, by hydrogenation 50 g of thienyl-2 acetonitrile in 200 ml of ethanol in the presence of 10 g of Raney nickel and 6 g of $CS_2CO_3$ under a pressure 23 and 50 bars (2.3 and 5 MPa). Yield 51.5%.

EXAMPLE 10 (Thienyl-2)-2 ethylamine 80 g of thienyl-2 acetonitrile, 120 ml of ethanol, 16 g of Raney nickel and 4 ml of a 10N solution of sodium hydroxide are introduced into a 500 ml autoclave. After hydrogenation at 50° C. under a pressure between 20 and 40 bars (2 and 4 MPa) the catalyst is filtered off and the solvent evaporated. The (thienyl-2)-2 ethylamine is distilled at 90° C./15 mm Hg (2 kPa). 46.6 g of the expected product is obtained. Yield 56.5%.

EXAMPLE 11 (Thienyl-2)-2 ethylamine 50 g of thienyl-2 acetonitrile, 200 ml of ethanol, 10 g of Raney nickel, 10 ml of water and 5 g of $K_2CO_3$ are introduced into a 500 ml autoclave. The mixture is hydrogenated at 50° C. under a constant pressure of 3 bars (300 kPa) until the absorption of hydrogen ends.

Analysis of the reactional medium by chromatography shows a yield of (thienyl-2)-2 ethylamine of 79%.

EXAMPLE 12 (Thienyl-2)-2 ethylamine

According to the process described in example 1, 31 g of (thienyl-2)-2 ethylamine is obtained, by hydrogenating 50 g of thienyl-2 acetonitrile in 200 ml of ethanol in the presence of 10 g of URUSHIBARA cobalt and under a pressure between 14 and 40 bars (1.4 and 4 MPa). Yield 60%.

EXAMPLE 13 (Thienyl-2)-2 ethylamine

According to the process described in example 1, 50 g of thienyl-2 acetonitrile is hydrogenated in 100 ml of methanol containing 100 ml Of liquid ammonia in the presence of 10 g of Raney nickel. The hydrogenation takes place at 50° C. under a pressure of between 31 and 55 bars (3.1 and 5.5 Mpa), until the theoretical quantity of hydrogen is absorbed. 37.8 g of (thienyl-2)-2 ethylamine is obtained. Yield 74%.

EXAMPLE 14 (Thienyl-2)-2 ethylamine 50 g of thienyl-2 acetonitrile, 200 ml of a mixture of ethanol and acetic acid in a ratio of 1 to 3 and 10 g of Raney nickel are introduced into a 500 ml hydrogenation autoclave. After hydrogenation at 50° C., under a pressure of between 8 and 32 bars (0.8 and 3.2 MPa), the catalyst is filtered off and the solvent evaporated. The residue is dissolved in the water, basified by the sodium hydroxide and extracted by ether. The ether is evaporated and the (thienyl-2)-2 ethylamine distilled. 26.3 g of the expected product is obtained. Yield 51%.

EXAMPLE 15 (Thienyl-2)-2 ethylamine

According to the process described in example 1, 18.7 g of thienyl-2 acetonitrile in hydrogenated in a mixture of acetic acid (225 ml) and ethanol (75 ml) in the presence of 1.8 g of $Ni_2B$. The reaction takes place at 65° C. under a pressure of between 24 and 31 bars (2.4 and 3.1 Mpa). When the absorption of hydrogen stops, the chromatography shows a yield of 75%.

EXAMPLE 16 (Thienyl-3)-2 ethylamine 50 g of thienyl-3 acetonitrile, 200 ml of ethanol, 2.5 ml of a 10N solution of sodium hydroxide and 10 g of Raney nickel are introduced into a 500 ml autoclave. The mixture is hydrogenated at 50° C. under a pressure of between 22 and 40 bars (2.2 and 4 MPa) until the theoretical quantity of hydrogen is absorbed. The catalyst is then filtered, the alcohol evaporated and the (thienyl-3)-2 ethylamine distilled at 95–100° C./15 mm Hg. 41.6 of the expected product is thus obtained. Yield 81%.

EXAMPLE 17 (Thienyl-3)-2 ethylamine 50 g of thienyl-3 acetonitrile, 200 ml of ethanol, 5 ml of water, 10 g of Raney nickel and 3 g of $K_2CO_3$ are introduced into a 500 ml hydrogenation autoclave. The mixture is hydrogenated at 50° C., under a pressure of between 20 and 40 bars (2 and 4 MPa) until the theoretical quantity of hydrogen is absorbed. The catalyst is filtered, the solvent evaporated and the (thienyl-3)-2 ethylamine distilled at 95–100/15 mm Hg. 35 g of the expected product is thus obtained. Yield 68%.

EXAMPLE 18 Di((thienyl-2)ehtyl)amine hydrochloride 50 g of thienyl-2 acetonitrile, 200 ml of ethanol and 10 g of Raney nickel is introduced into a 500 ml autoclave. The mixture is hydrogenated at 50° C. under a pressure between 17 and 50 bars (1.7 and 5 MPa) until the theoretical quantity of hydrogen is absorbed. The catalyst is filtered off, the solvent evaporated and the residue dissolved in 200 ml of 2N hydrochloric acid. The hydrochloride of the insoluble secondary amine is filtered, rinsed with acetone and dried at 50° C. to constant weight. 43.2 g of di((thienyl-2)-2 ethyl)amine hydrochloride is obtained, m.p.=244° C. with decomposition from 220° C., correct element analysis, Yield 79%.

EXAMPLE 19 Di((thienyl-3)-2 ethyl) amine and (thienyl-3)-2 ethylamine 50 g of thienyl-3 acetonitrile, 200 ml of ethanol and 10 g of Raney nickel is introduced into a 500 ml autoclave. The mixture is hydrogenated at 50% under a pressure between 20 and 40 bars (2 and 4 MPa) until the theoretical quantity of hydrogen is absorbed. The catalyst is filtered off, the solvent is evaporated and the residue is distilled with a water-jet pump and then with a vane pump. 4.5 g of (thienyl-3)-2 ethylamine is obtained which distils at 95–100° C. under 15 mm of Hg (yield 9%) and 37.05 g of di((thienyl-3)0-2 ethyl)amine which distils at 128°–135° C./3 mm Hg (400 Pa) (yield 78 %). The di((thienyl-3)-2 ethyl) amine is characterised by NMR of the proton ( =2.8, 6.8, 7.1 ppm, NH at 1.1 ppm in CDCL$_3$) and of carbon 13 (-CH$_2$CH$_2$-N at 30.7 ppm, -Ch$_2$CH$_2$N at 50.1 ppm, methines of thiophene at 121, 125 and 128 ppm, carbon substituted in position 3 at 140.4 ppm in CDCL$_3$).

EXAMPLE 20 (Thienyl-3)-2 ethylamine and di((thienyl-3)-2 ethyl)amine

According to the process described in example 19, 50 g of thienyl-3 acetonitrile is hydrogenated at 50° C. in 200 ml of dioxan, in the presence of 10 g of Raney nickel under a pressure between 21 and 56 bars (2.1 and 5.6 MPa) until the theoretical quantity of hydrogen is absorbed. 38.3 g of di((thienyl-3)-2 ethyl)amine (yield 80.5%) and 6.6 g of (thienyl-3)-2 ethylamine (yield 13%) are obtained.

EXAMPLE 21 (Di(thienyl-3)-2 ethyl)amine and (thienyl-3)-2 ethylamine

According to the process described in example 19, 50 g of thienyl-3 acetonitrile is hydrogenated in 200 ml of tetrahydrofuran in the presence of 7 g of triethylamine and 10 g of Raney nickel under a pressure between 20 and 40 bars (2 and 4 MPa), 35 g of di(thienyl-3)-2 ethyl)amine (yield 74%) is thus obtained and 9.4 g of (thienyl-3)- ethylamine. Yield 18%.

EXAMPLE 22 Di((thienyl-2 ethyl)amine

Proceeding as in example 19, by hydrogenating 50 g of thienyl-2 acetonitrile in 200 ml of ethanol in the presence of Raney nickel under a pressure between 20 and 40 bars (2 and 4 MPa), 38 g of di((thienyl-2)-2-ethylamine is obtained. b.p : 125–130° C./2 mm Hg. Yield 80 %.

EXAMPLE 23 (Thienyl-2)-2 ethylamine and di((thienyl-2)-2 ethyl)amine

Proceeding as in example 1, by hydrogenating 50 g of thientyl-2 acetonitrile in 200 ml of ethanol at 95 % in an aqueous solution in the presence of 3 g of K$_2$CO$_3$ and 10 g of Raney nickel under a constant pressure of 12 bars (1.12 MPa) and at 25° C., 40.3 g of (thienyl-2)-2 ethylamine is obtained. Yield 78.0%.

EXAMPLE 24:

Proceeding as in example 1 by hydrogenating 50 g of thienyl-2 acetonitrile in 200 ml of ethanol at 95% in aqueous solution in the presence of 3 g of K$_2$CO$_3$ and 5 g of Raney nickel under a constant pressure of 20 bars (2 MPa) and at 40° C., 39.9 g of (thienyl-2)-2 ethylamine is obtained. Yield 77%.

EXAMPLE 25:

0.6 1. of ethanol at 95% in aqueous solution is introduced into a 3.5 1. hydrogenator. The hydrogen pressure is established at 20 bars (2 MPa) and the temperature at 50° C. Using a dosing pump a solution of 200 g of thienyl-2 acetonitrile is introduced over 8 hours into 1 litre of ethanol at 95% in aqueous solution.

When all the hydrogen absorption has finished. the catalyst is filtered off, the solvent evaporated and the (thienyl-2)-2 ethylamine is distilled. 146.7 g of the expectd product is obtained. Yield 71%.

What is claimed is:

1. A process for the preparation of thienylethylamines of the formula R-NH-R′, in which R represents

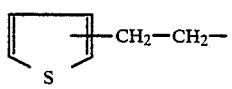

and R′ represents H or the radical R, comprising subjecting a solution of a thienyl-acetonitrile of the formula

to a hydrogenation in the presence of a Raney nickel catalyst and a mineral or organic base, at a pressure between $10^5$ and $10^7$ Pa, and at a temperature between 15° C. and 80° C.

2. Process according to claim 1, wherein the reaction takes place in an aliphatic alcohol.

3. Process according to claim 1, wherein the concentration of the nitrile in the reactional medium is between 20 and 40% (w/v) and that of the catalyst is between 2 and 30% by weight in ratio to the substrate.

4. Process according to claim 1, wherein the pressure is betwen 1 and 6 MPa.

5. Process according to claim 1, wherein the base is chosen from NaOH, LiOH and K$_2$CO$_3$.

6. Process according to claim 1, wherein the base is chosen from NH$_3$, KOH, Cs$_2$CO$_3$ and HON (R$_1$)4 in which R$_1$ represents a C$_1$ to C$_4$ alkyl.

7. Process according to claim 1, wherein the base is used in quantities varying from 0.1 to 15% in ratio to the quantity of thienyl-acetonitrile employed.

* * * * *